United States Patent [19]

Schick

[11] Patent Number: 5,482,628
[45] Date of Patent: Jan. 9, 1996

[54] COLUMN FOR LIQUID CHROMATOGRAPHY

[75] Inventor: Hans G. Schick, Anacortes, Wash.

[73] Assignee: Upchurch Scientific, Inc., Oak Harbor, Wash.

[21] Appl. No.: 277,853

[22] Filed: Apr. 15, 1994

[51] Int. Cl.⁶ .................................................. B01D 15/08
[52] U.S. Cl. ........................................ 210/198.2; 210/656
[58] Field of Search .................................... 210/635, 656, 210/198.2, 541, 232, 238; 96/101, 104, 106

[56] References Cited

U.S. PATENT DOCUMENTS

| | | | |
|---|---|---|---|
| 3,583,230 | 6/1971 | Patterson | 210/198.2 |
| 3,682,315 | 8/1972 | Haller | 210/198.2 |
| 3,763,879 | 10/1973 | Jaworek | 210/198.2 |
| 3,855,130 | 12/1974 | Randau | 210/198.2 |
| 3,878,099 | 4/1975 | Ogle | 210/198.2 |
| 3,904,527 | 9/1975 | Wilhelmson | 210/198.2 |
| 3,926,800 | 12/1975 | Stephens | 210/198.2 |
| 4,093,550 | 6/1978 | Stahl | 210/198.2 |
| 4,187,177 | 2/1980 | Stahl | 210/198.2 |
| 4,283,280 | 8/1981 | Brownlee | 210/198.2 |
| 4,293,415 | 10/1981 | Bente | 210/198.2 |
| 4,313,828 | 2/1982 | Brownlee | 210/198.2 |
| 4,389,313 | 6/1983 | Charney | 210/198.2 |
| 4,451,364 | 5/1984 | Higgins | 210/198.2 |
| 4,522,715 | 6/1985 | Walters | 210/198.2 |
| 4,563,275 | 1/1986 | McEachern | 210/198.2 |
| 4,565,631 | 1/1986 | Hatch | 210/198.2 |
| 4,587,014 | 5/1986 | America | 210/198.2 |
| 4,737,284 | 4/1988 | Haucke | 210/198.2 |
| 4,755,293 | 7/1988 | Sakamoto | 210/198.2 |
| 4,758,340 | 7/1988 | Marchand | 210/450 |
| 4,769,141 | 9/1988 | Coyillard | 210/198.2 |
| 4,784,772 | 11/1988 | Gotoh | 210/638 |
| 4,861,473 | 8/1989 | Shackelford | 210/198.2 |
| 4,876,005 | 10/1989 | America | 210/198.2 |
| 4,968,421 | 11/1990 | Spacek | 210/198.2 |
| 5,131,818 | 7/1992 | Wittkop | 417/273 |
| 5,169,522 | 12/1992 | Shalon | 210/198.2 |
| 5,194,225 | 5/1993 | Muller | 210/198.2 |
| 5,238,556 | 8/1993 | Shirkhan | 210/656 |

OTHER PUBLICATIONS

Supelco, Inc., "Tech Novations" magazine, issue 1 (printed Sep., 1992), p. 6.
Upchurch Scientific, Inc., "Catalog of Chromatography and Fluid Transfer Fittings" (1993), pp. 84, 89.
Upchurch Scientific, Inc., "Chromatography Fittings and Accessories Catalog and Technical Reference Manual" (1992), pp. 84, 89.
Alltech Associates, Inc., "Chromatography Fittings and Accessories" bulletin 275 (1994), p. 9.
Alltech Associates, Inc., "Chromatography" catalog 300 (1993), pp. 191, 428, 628, 630, 667.
Alltech Associates, Inc., "Ion Chromatography Accessories and Instrumentation" bulletin 217 (1992), p. 36.
Phase Separations, Inc. "HPLC Columns and Accessories" catalog, part number 971001 (1990), p. H22.

Primary Examiner—Ernest G. Therkorn
Attorney, Agent, or Firm—Vinson & Elkins

[57] ABSTRACT

A biocompatible column for use in liquid chromatography applications includes a biocompatible, polymeric inner tube which is located within a metallic outer tube. The column has biocompatible end fittings which extend beyond the ends of the outer tube. The ends of the outer tube are tapered to extend radially inward towards the longitudinal axis of the column to secure the end fittings and the inner tube in place relative to the outer tube. Alternatively, one or more biocompatible frits are included in seats in the end fittings. A passageway through the inner tube is packed with any one of a number of various packing materials. The present invention may comprise either a guard column or an analytical or preparative column. A liquid chromatography system in which the column of the present invention is used is also described.

18 Claims, 3 Drawing Sheets

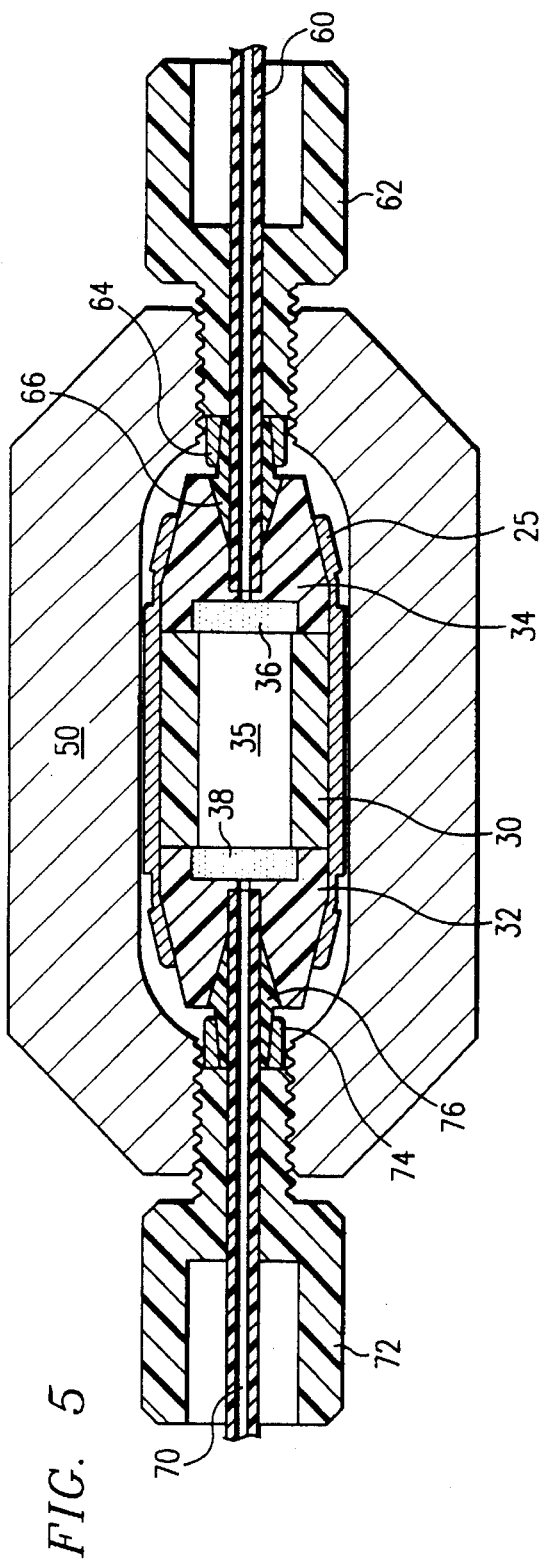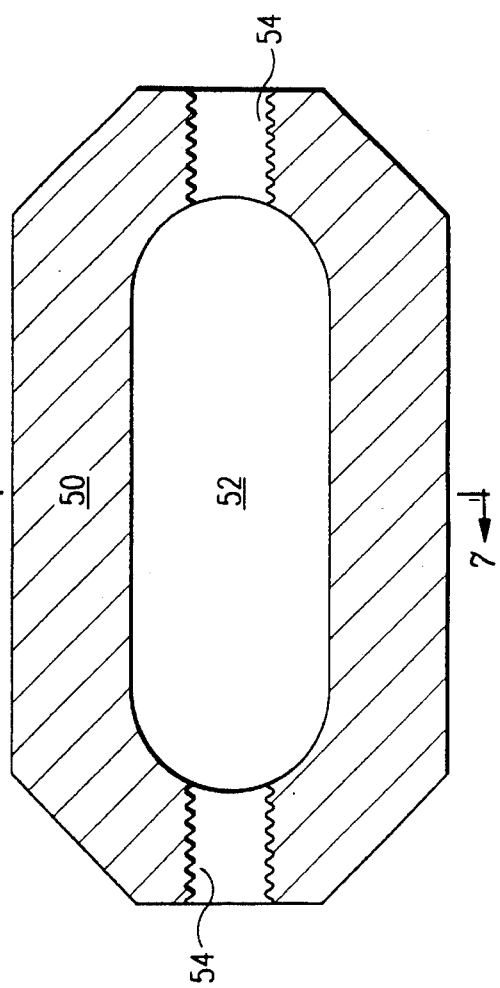

COLUMN FOR LIQUID CHROMATOGRAPHY

FIELD OF THE INVENTION

This invention relates generally to an improved column for use in liquid chromatography applications, and relates more particularly to a column well-suited for applications involving relatively high pressures and/or requiring biocompatibility.

BACKGROUND OF THE INVENTION

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components. A more detailed description of the separation process can be found, among other places, in Chapters 2 and 5 of *Introduction to Modem Liquid Chromatography* (2d ed. 1979) by L. R. Snyder and J. J. Kirkland, which chapters are incorporated by reference herein.

Once the sample (with its components now separated) leaves the column, it flows with the mobile phase past a detector. The detector detects the presence of specific molecules or compounds. As discussed in Chapter 4 of *Introduction to Modem Liquid Chromatography*, which chapter is incorporated by reference herein, two general types of detectors are used in LC applications. One type measures a change in some overall physical property of the mobile phase and the sample (such as their refractive index). The other type measures only some property of the sample (such as the absorption of ultraviolet radiation). In essence, a typical detector in an LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, an LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might other, vise bind irreversibly to the analytical or preparative column.

It will be understood to those skilled in the art that, as used herein, the term "LC system" is intended in its broad sense to include all apparatus used in connection with liquid chromatography, whether made of only a few simple components or made of numerous, sophisticated components which are computer controlled or the like.

Many different types of LC systems and components for LC systems are commercially available from a number of vendors. For example, Millipore Corporation of Milford, Mass., Beckman Instruments of Fullerton, Calif., and Hewlett-Packard Co. of Palo Alto, Calif., all sell LC systems, including pumps, sample injection valves, columns, and detectors, among other things. In addition, various columns with various packings are commercially available from a variety of sources, including (among others) Upchurch Scientific, Inc., of Oak Harbor, Wash., and Baxter Healthcare Corporation of Deerfield, Ill.

Today, most LC systems include pumps which can generate relatively high pressures of up to around 6,000 psi. In many situations, an operator can obtain successful results by operating an LC system at "low" pressures of anywhere from just a few psi or so up to 1,000 psi or so. More often than not, however, an operator will find it desirable to operate an LC system at relatively "higher" pressures of over 1,000 psi. The operation and use of LC systems at such "higher" pressure levels is often referred to as "high pressure liquid chromatography" or "high performance liquid chromatography" (HPLC).

In order to be suitable for HPLC applications, a column must be made to withstand the typical operating pressures of the LC system. If the column is too weak, it may burst and thereby leak. Given the types of solvents that are sometimes used as the mobile phase and the expense of obtaining and/or preparing many samples for use, any such failure is a serious concern. Besides being able to withstand such pressures, the column must be made of a material which can withstand the chemical action of the mobile phase; i.e., the ideal column is chemically inert to the mobile phase used. In addition, the column needs to be durable so that it has a commercially useful life span.

Given such concerns, conventional columns typically consist of a stainless steel tube which had stainless steel end fittings attached at each end. Often, such columns were "packed" with appropriate materials to achieve the chemical separation required. A detailed discussion of end fittings, and column end fittings in particular, can be found in Chapter VII of the booklet *HPLC Fittings* (2d ed. 1992) by Paul Upchurch, which chapter is incorporated by reference herein. Typical column end fittings must hold to operating pressures of up to 6,000 psi or so. Such conventional column end fittings usually have been machined from stainless steel. The end fittings also must be suitable for connecting the column to the tubing used in the LC system to connect the various elements of the LC system with one another.

The inside diameter of the column must be polished in order to eliminate the possible adverse effects a rough inside wall may have on the separation process. It has been suggested that the smoothness of the inside wall of the column influences the homogeneity of the packing. Hence, a smoother surface finish on the column's inside surface results in a better level of performance from the column. Accordingly, most conventional columns typically consist of a stainless steel tube with a highly polished inside diameter surface finish. Although such a polished finish is important, it requires additional manufacturing steps and can be expensive to obtain.

More recently, it has been realized that the use of stainless steel components in an LC system have potential drawbacks in situations involving biological samples. For example, the components in a sample may attach themselves to the wall of a stainless steel column. This presents problems because the detector's measurements (and thus the chromatogram) of a given sample may not accurately reflect the sample if some of the sample's ions remain in the column and do not pass the detector. Perhaps of even greater concern, however, is the fact that ions from the stainless steel column may detach from the column and flow past the detector, thus leading to potentially erroneous results. Hence, there is a need for a "biocompatible" column; i.e., a column made of a material which is chemically inert with respect to such "biological" samples and the mobile phase used with such samples so that ions will not be released by the column and thus contaminate the sample. It will be understood that the use of the term "column" herein applies to analytical and preparative columns, and also applies to guard columns and the like.

To avoid biocompatibility problems, glass lined columns which have an exterior made of stainless steel are known. Because such columns are prone to breakage, a great deal of care in the manufacture, transportation, handling, and use of such columns is required. Moreover, it has been observed that the use of such glass-lined columns at high pressures is not appropriate.

Columns using extruded rods or tubing made of the polymer polyetheretherketone (PEEK) with molded or machined PEEK column end fittings are also known, but because of their lack of strength, such columns are typically limited to applications using fairly low pressures (i.e., pressures of not more than 200 psi or so), although some columns with larger walls have been claimed to work at up to 2,000 psi or so. Columns made of the polymer PEEK are also known, but such columns are machined from large diameter PEEK rods. In order to produce such PEEK columns in this way, the PEEK tube must first be machined and then its inside diameter must be polished. This approach thus involves additional manufacturing steps which add additional costs. Also, the surface finish obtained in such columns, while acceptable for many LC applications, is often unacceptable for applications where high levels of performance are required of the column. Moreover, to hold to the high pressures at which many columns are packed and at which some LC systems operate, such PEEK columns must be made with a very thick wall.

Another conventional column includes a PEEK tube surrounded by an aluminum jacket. However, the use of PEEK tubes still requires the extra manufacturing costs and therefore added time and expense. In addition, the surface finish obtained via such an approach may not be acceptable for LC applications requiring high performance by the column. Such columns also require the use of specialized, metallic end fittings which can handle the higher pressures but which require the use of additional polymeric pieces to ensure biocompatibility. The use of such additional pieces results in a higher chance that a connection between some of the pieces will leak or fail, an obviously undesirable result. The additional pieces and joints in such columns also may decrease the durability of such columns.

Therefore, it is an object of the present invention to provide a biocompatible column which can be used in relatively high pressure LC applications and which has sufficient strength for use in relatively high pressure LC applications.

It is yet another object of the present invention to provide a biocompatible column which is not fragile and which does not require excessive manufacturing steps or costs.

It is still another object of the present invention to provide a biocompatible column which is easily connected or disconnected.

It is still another object of the present invention to provide a biocompatible column with a highly polished inside surface and with a minimal number of pieces.

It is still another object of the present invention to provide a durable, biocompatible column which can provide a high level of performance at relatively high pressures with a minimal chance of leakage.

The above and other advantages of the present invention will become readily apparent to those skilled in the art from the following detailed description of the present invention, and from the attached drawings, which are briefly described below.

SUMMARY OF THE INVENTION

The present invention may be implemented as a metal tube to provide an outer column jacket, within which a biocompatible, polymeric tube, one or more frits, and appropriate end fittings are located. The ends of the outer metal jacket are tapered inwardly at each end of the column. Thus, the inner diameter of the outer jacket is reduced at each end of the column to snugly hold the respective end fittings (and the frits and the inner tube held between the end fittings) in place and prevent leakage. The outer metal tube provides sufficient strength to allow the column to operate at relatively high pressures. At the same time, however, the polymeric inner tube and the end fittings present only chemically inert surfaces for contact with the mobile phase and sample, thus providing biocompatibility. As a whole, such a column can operate at the relatively higher pressures associated with the use of conventional metal columns, yet provide the biocompatibility associated with polymeric materials.

BRIEF DESCRIPTION OF THE DRAWINGS

FIG. 5 is a cross-sectional view of a column in accordance with the present invention connected to tubing and held within a cartridge holder.

FIG. 6 is a cross-sectional view of a cartridge holder.

DETAILED DESCRIPTION OF THE INVENTION

Figure 1:
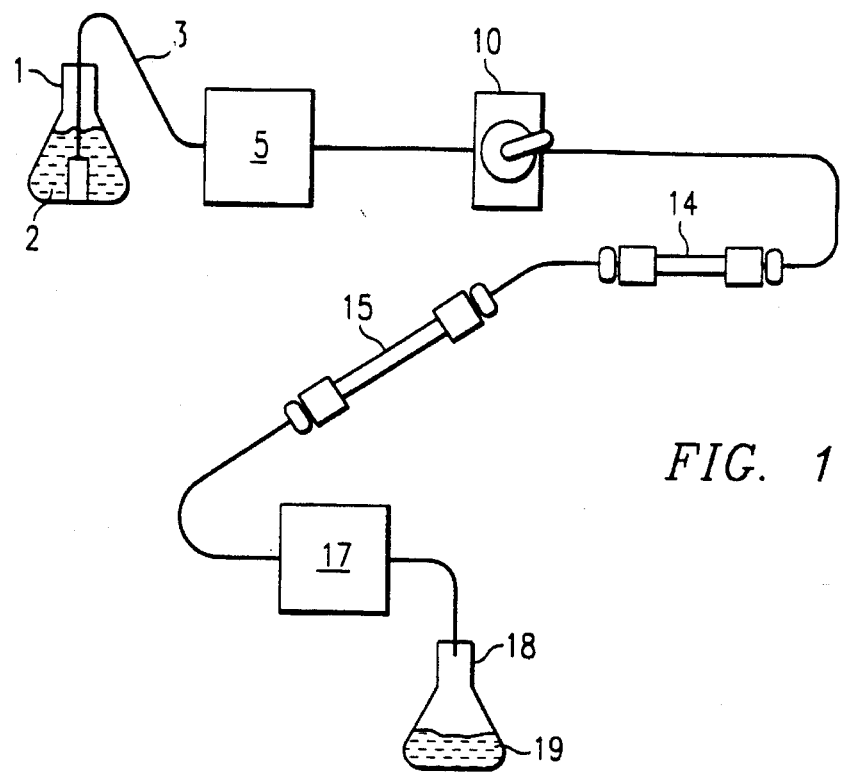
FIG. 1 is a block diagram of a conventional LC system.

In FIG. 1, a block diagram of the essential elements of a conventional LC system is provided. A reservoir 1 contains a solvent or mobile phase 2. Tubing 3 connects the mobile phase 2 in the reservoir 1 to a pump 5. The pump 5 is connected to a sample injection valve 10 which, in turn, is connected via tubing to a first end of a guard column 14. The second end of the guard column 14 is in turn connected to the first end of a primary column 15. The second end of the primary column 15 is then connected via tubing to a detector 17. After passing through the detector 17, the mobile phase 2 and the sample injected via injection valve 10 are expended into a second reservoir 18, which contains the chemical waste 19. As noted above, the sample injection valve 10 is used to inject a sample of a material to be studied into the LC system. The mobile phase 2 flows through the tubing 3 which is used to connect the various elements of the LC system together.

When the sample is injected via sample injection valve 10 in the LC system, the sample is carried by the mobile phase through the tubing into the column 15. As is well known in the art, the column 15 contains a packing material which acts to separate the constituent elements of the sample. After exiting the column 15, the sample (as separated via the column 15) then is carried to and enters a detector 17, which detects the presence or absence of various chemicals. The information obtained by the detector 17 can then be stored and used by an operator of the LC system to determine the constituent elements of the sample injected into the LC system.

Figure 2:
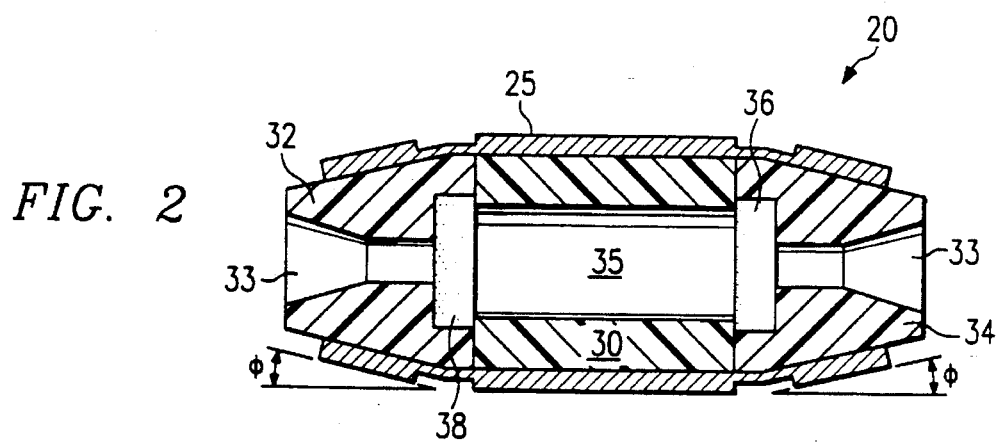
FIG. 2 is a cross-sectional view of a column in accordance with the present invention.

Referring now to FIG. 2, a cross-sectional view of a column 20 in accordance with the present invention is shown. The column 20 consists of an outer tube 25 surrounding an inner tube 30. As shown in FIG. 2, the inner tube 30 has a passageway 35 extending along the longitudinal axis therethrough. Column 20 also includes end fittings 32 and 34 at its ends. As seen in FIG. 2, a portion of each of the end fittings 32 and 34 extends beyond the first and second ends of the outer tube 25, respectively. Because the outer diameter of at least a portion of each of the end fittings 32 and 34 (i.e., the outer diameter of the end fittings 32 and 34 where they abut the ends of the inner tube 30) exceeds at least a portion of the inside diameter of the outer tube 25 (i.e., the inside diameter of the ends of the outer column 25), the end fittings 32 and 34 cannot be pulled through and hence separated from the outer tube 25. In short, the end fittings 32 and 34 prevent the inner tube 30 and the outer tube 25 from longitudinally moving more than a short distance relative to one another. Each of the end fittings 32 and 34 has a funnel-shaped counterbore 33. The counterbores 33 are provided in order to allow appropriate fittings (shown in FIG. 7) to be removably attached to the column 20.

The outer tube 25 can be made of almost any metal. For best results, I prefer to use a seamless 316 stainless steel tube, although aluminum and other metals may be used. The metallic outer tube 25 provides support and strength to the column 20, thereby ensuring that the column 20 can be used in high pressure liquid chromatography applications and can be packed with a packing material (not shown in FIG. 2) at pressures of up to about 8,000 psi.

Before use in LC applications, the passageway 35 of the column 20 is filled with any one of a number of packing materials (not shown in FIG. 2). It will be apparent to those skilled in the art how the passageway 35 can be packed with appropriate packing materials. As discussed below, any one of a number of different packing materials may be used. Once packed with an appropriate packing material, the column 20 can be used in operation in an LC system at relatively high operating pressures of up to around 3,000 to 5,000 psi or so. In testing, the column 20 has withstood pressures of over 8,000 psi without leaking or failure.

At the first and second ends of the column 20 are column end fittings 32 and 34, respectively. As shown in FIG. 2, the inner ends of the column end fittings 32 and 34 are located adjacent to and abut the outer ends of the inner tube 30. As can be seen from FIG. 2, the outer end portions of the outer tube 25 taper inwardly towards the longitudinal axis of the column 20. The taper angle $\phi$ is shown on FIG. 2; the angle $\phi$ measures the angle between the tapered, outer ends of the column 20 and a line parallel to the longitudinal axis of the column 20 and defined by the non-tapered central body of the column 20. The tapered ends of the outer tube 25 thus press the end fittings 32 and 34 against the outer ends of the inner tube 30. For best results, I prefer that each end of the outer tube 25 have a taper angle $\phi$ of about 13°, as measured by the line defined by the outer surface of the central, non-tapered body of the column 20. From FIG. 2, it can be observed that if the taper angle $\phi$ is too small, the tapered ends of the outer tube 25 will not exert as much force on the end fittings 32 and 34 as may be necessary to allow the column 20 to withstand high operating pressures. At the same time, however, a larger taper angle $\phi$ will require that the walls of the end fittings 32 and 34 near the ports 33 be thinner and thus may not be able to withstand the high operating pressures desired. In addition, too much of a taper angle $\phi$ may cause radial compression of the flits 38 and 36, this presenting the possibility of a failure by a flit. As noted, I prefer that the taper angle $\phi$ of each end of the column 20 be the same, but this is not required.

Preferably, the end fittings 32 and 34, as well as the inner tube 30, are made of the synthetic polymer polyetheretherketone, which is commercially available under the trademark "PEEK" from ICI Americas. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth counterbores 33.

Although the polymer PEEK is substantially chemically inert with respect to most solvents used as the mobile base for LC applications, there are a few solvents which may cause PEEK to swell. Such solvents include dimethylsulfoxide, methylene chloride, and tetrahydrofuran. In addition to its other advantages, the use of the metallic outer tube 25 helps prevent and control the swelling which may be caused by the use of such solvents. In situations where an operator wants to use a solvent to which PEEK is not chemically inert, such as concentrated nitric acid or sulfuric acid as the mobile phase, a column 20 with an inner tube 30 and end fittings 32 and 34 made of PEEK is not appropriate due to the reaction of PEEK to concentrated nitric acid and sulfuric acid. Other chemically inert synthetic polymerics, such as TEFZEL, polytetrafluoroethylene (which is sold by DuPont under the trademark "TEFLON") or chlorotetrafluoroethylene (which is sold by 3M under the trademark "KEL-F"), or the polyimid sold under the trademark VESPEL can be used to form the inner tube 30 and the end fittings 32 and 34.

With reference to FIG. 2, it can be seen that the outer surface of the inner tube 30 is adjacent to and contacts the inner surface of the metallic outer tube 25. The outer surface of the inner tube 30 need not be attached to the inner surface of the outer tube 25, as the end fittings 32 and 34 (which are held in place by the tapered ends of outer tube 25) prevent anything more than a relatively modest amount of longitudinal movement between inner tube 30 and outer tube 25 relative to one another. Hence, the end fittings 32 and 34 secure the body of the inner tube 30 within the outer tube 25 and prevent the removal of the inner tube 30 from the outer tube 25.

Still referring to FIG. 2, the column 20 is shown in a cross-sectional view as assembled with frits 36 and 38. Porous disks (or frits) 36 and 38 are used for filtering the mobile phase and the sample as they move through an LC system. The frits 36 and 38 can be of a type which is commonly known and commercially available from Upchurch Scientific, Inc., of Oak Harbor, Wash. Frits 36 and 38 may be made of biocompatible materials such as titanium or PEEK. For best results, we prefer to use biocompatible flits 36 and 38 made of the polymer PEEL which are commercially available from Upchurch Scientific, Inc., of Oak Harbor, Wash. As noted above with respect to the end fittings 32 and 34 and the inner tube 30, however, the use of frits 36 and 38 made of PEEK may not be appropriate depending on the solvent to be used. Hence, the flits 36 and 38 may be made of other biocompatible materials, such as titanium or ultra-high molecular weight polyethylene.

Figure 3:
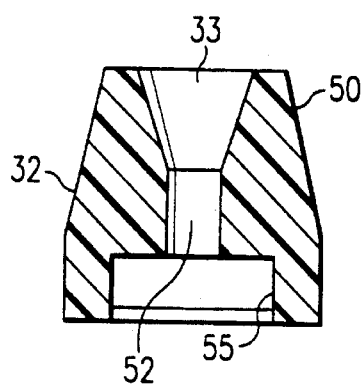
FIG. 3 is a cross-sectional view of an end fitting of the column of the present invention.
Figure 4:
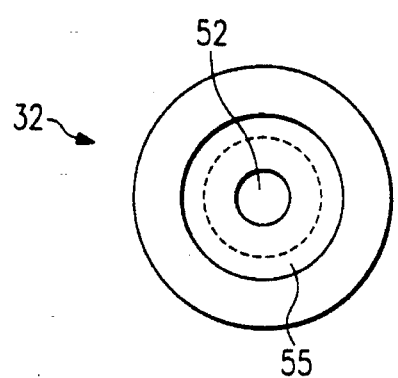
FIG. 4 is an end view of one end of an end fitting of the column of the present invention.

Referring now to FIGS. 3 and 4, an end fitting 32 is shown. (In the preferred embodiment, end fittings 32 and 34 are interchangeable with each other.) As shown in FIG. 3, end fitting 32 has a tapered first end 50, within which a counterbore 33 is located. At its second end, the end fitting 32 has a seat 55, which is adapted to receive and hold a flit 38 (as shown in FIG. 2). As also shown in FIG. 3, a passageway 52 extends through the body of end fitting 32, thereby allowing fluid communication therethrough. Although not shown, it should be noted that the counterbore 33 could be threaded to allow connection to tubing through the use of a conventional combination of a ferrule and nut (not shown). In the preferred embodiment, however, the counterbore 33 is tapered to form a generally conical or funnel shape, which ends at one end of the passageway 52. This allows the column 20 to be easily connected in an LC system (as shown in FIG. 5).

Referring now to FIG. 5, column 20 is shown connected to tubing 60 and tubing 70 at the first and second ends, respectively, of the column 20. In FIG. 5, the column 20 is positioned within a cartridge holder 50. The first end of the column 20 is connected to the tubing 60 through the use of a ferrule 66, a metal ring 64, and a male nut 62. As is well known to those skilled in the art, the ferrule 66, ring 64, and male nut 62 all can be slid onto the end of the tubing 60 prior to the placement of the tubing 60 in the counterbore 33. The tubing 60 is then positioned so that the end of the tube 60 is flush against the bottom of the passageway 52 in the end fitting 34. The ferrule 66 fits within the counterbore 33 of the end fitting 34. The ferrule 66 is secured in place by threading the male nut 62 into the cartridge holder 50. This forces the ring 64 against the ferrule 66, which in turn presses the female 66 against the counterbore 33 of the end fitting 34, thus providing a leak-free seal between the end fitting 34 and the tubing 60. As shown in FIG. 5, a second piece of tubing 70 is attached to the second end of the column 20 by a similar combination of a male nut 72, a metal ring 74, and a ferrule 76. The male nut 72 is screwed into the second end of the cartridge holder 50, thereby forcing the metal ring 74 and thus the ferrule 76 against the end fitting 32, creating a leak-free seal between the tubing 70 and the end fitting 32. For best results, I prefer to use ferrules 66 and 76 made of PEEK, metal rings 64 and 74 made of 316 stainless steel, and male nuts 62 and 72 made of PEEK. The combination of a male nut 62, metal ring 64, and ferrule 66 are commercially available from Upchurch Scientific, Inc., of Oak Harbor, Wash., under the trademark "LITETOUCH."

Figure 7:
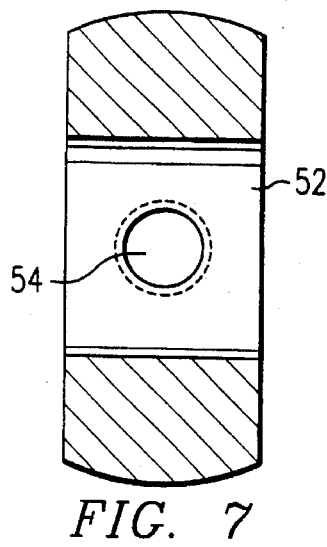
FIG. 7 is a cross-sectional view of the cartridge holder taken along line 7—7.

Referring now to FIGS. 6 and 7, the cartridge holder 50 is shown in greater detail. In FIG. 6, a cross-sectional view of the cartridge holder 50 is shown. The cartridge holder 50 has a hollow, interior area 52 which is adapted to hold the column 20. Obviously, the size of the interior area 52 and the size and length of the cartridge holder 50 will depend on the width and length of the column 20 which is to be held within the interior area 52 of a given cartridge holder 50. The cartridge holder 50 also has threaded bores 54 which extend from outside the cartridge holder 50 to the interior area 52. For best results, I prefer to use a cartridge holder 50 made of aluminum. However, it will be obvious to those skilled in the art that the cartridge holder may be made of any other appropriate metal, such as steel or the like. Similarly, the cartridge holder 50 may be made of PEEK or another appropriate polymer. However, the cartridge holder 50 must be of a sufficiently strong material so that the threads in the bores 54 are strong enough to hold the male nuts 62 and 72 (as shown in FIG. 5) at the relatively high pressures in which the column 20 will be used when the column 20 is connected by tubing 60 and tubing 70 to a LC system (not shown). Of course, the shape of the cartridge holder 50 may vary significantly, so long as the cartridge holder 50 is sufficiently strong to allow a leak-free connection between the tubing 60 and tubing 70 and the column 20 when assembled as shown in FIG. 5.

A brief description of the method by which a column 20 is made should help provide a better understanding of the invention. First, the appropriate components are gathered. An inner tube 30 and an outer tube 25 of appropriate sizes are obtained. (As shown in FIG. 2, the outside diameter of inner tube 30 is preferably quite close in size to the inside diameter of the outer tube 25.) Next, appropriate flits 36 and 38 are placed in the seats 55 of the end fittings 34 and 32, respectively.

Figure 8:
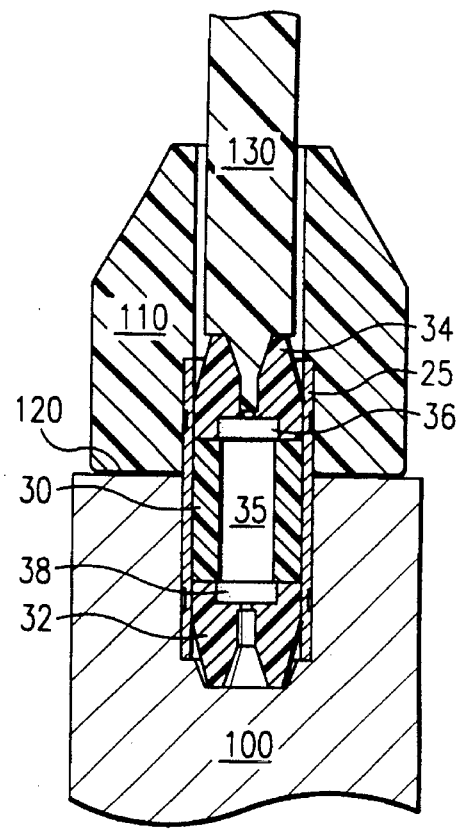
FIG. 8 is a cross-sectional view of the assembly of the column through the use of an anvil and a press.

One end of the outer tube 25 is placed into an anvil 100. The anvil 100 is adapted to receive and hold at least a portion of the outer tube 25 as shown in FIG. 8. Next, a centering collar 110 is positioned around the outer tube 25.

The combination of a flit 38 and an end fitting 32 is then placed on top of the outer end of the outer tube 25 extending out of the anvil 100. The fitting 32 is placed so that its tapered end faces down towards the anvil 100. Because the outside diameter of the end fitting 32 at the end opposite the port 33 is slightly larger than the inside diameter of the outer tube 25, the end fitting 32 sits on top of the outer tube 25. The inner tube 30 is then placed on top of the end fitting 32. The passageway 35 of the inner tube 30 will be packed prior to the assembly of the column 20. The packing (not shown) may be inserted into the inner tube 30 through any one of a number conventional techniques.

After the inner tune 30 has been positioned on top of the end fitting 32, the combination of frit 36 and end fitting 34 is placed on top of the inner tube 30 so that the frit 36 is adjacent to the end of the inner tube 30. Next, an appropriate press 130 is lowered by means of a conventional press (not shown). The press 130 is pressed into and against the outer end of the end fitting 34, forcing the inner tube 30 and the end fittings 32 and 34 into the outer tube 25 to the position shown in FIG. 8.

Figure 9:
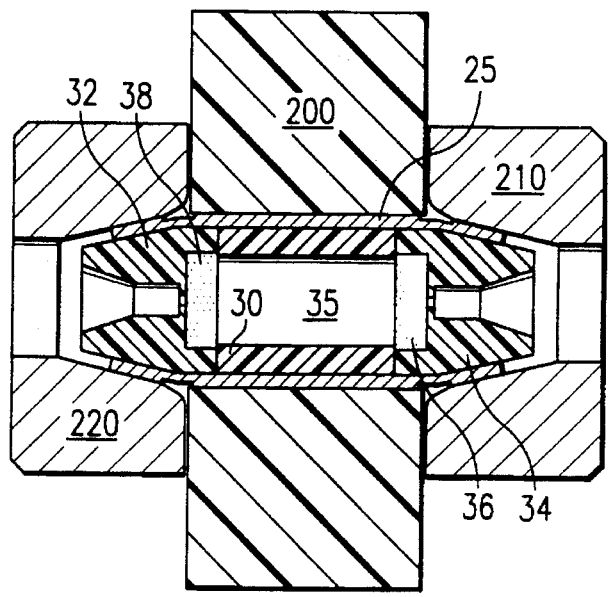
FIG. 9 is a cross-sectional view of the column as made with the use of a holder and two crimping dies to crimp the outer ends of the outer tube.

The column 20 is then removed and is placed in another press (not shown) to crimp the outer ends of the outer tube 25. Although the details of the crimping operation are not necessary, an overview is helpful. The column 20 is placed in appropriate holder 200 as shown in FIG. 9. The outer ends of the column 20 extend beyond holder 200. Opposing crimping dies 210 and 220 are pressed over and against the outer ends of the column 20 by a conventional press (not shown). As seen in FIG. 9, the crimping dies 210 and 220 are shaped so that, as they move towards the holder 200 and against the outer ends of the column 20, they crimp the outer ends of the column 20 to the desired taper angle φ. As shown in FIG. 9, the crimping dies 210 and 220 deform the outer ends of the outer tube 25 so that the outer ends of the outer tube 25 are tapered inwardly towards the longitudinal axis of the column 20. As noted above, a taper angle φ of 13° from a line defined by the outer surface of the central body of the column 20 and parallel to the longitudinal axis of the column 20 has been found preferable.

EXAMPLE

The following describes only one possible specific embodiment of my invention, and is not to be considered as limiting the scope of the claims. Referring back to FIG. 2, an appropriate guard column 20 can be described as follows: The length of the column 20 (i.e., the length of the packed bed which is located in the passageway 35) is 10 mm (not including frits 36 and 38 or end fittings 32 and 34). The diameter of the passageway 35 in the column 20 is 4.6 mm. The outer tube 25 is made of 316 stainless steel and the inner tube 30 is made of the polymer PEEK. The ends of the outer column 25 are tapered inwardly towards the longitudinal axis of the column 20, with the taper angle φ being about 13°. In addition, the passageway 35 of the column 20 is packed with one of a variety of well-known packing materials, such as any one of the following: C-18, C-8, or silicon. End fittings 32 and 34 are made of PEEK as well. The frits 36 and 38 are also made of PEEK, although they could be made of ultra-high molecular weight polyethylene or titanium.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiments and specific forms, materials, and the like are merely illustrative and do not limit the scope of the invention or the claims herein.

I claim the following:

1. A column for liquid chromatography which comprises:

an outer metal tube having first and second ends;

a biocompatible inner tube having a passageway therethrough sized and dimensioned for retaining chromatographic packing material and having first and second ends, wherein said inner tube is located within said outer metal tube; and first and second biocompatible end fittings that allows for connection to a chromatography system each having a passageway therethrough and each having a first and second end, wherein the first end of each of said end fittings abuts an end of said inner tube and the second end of each of said end fittings extends beyond an end of said outer tube, and wherein the ends of the outer tube are tapered inwardly towards the longitudinal axis of the outer tube at an angle sufficient to hold said first and second end fittings in place and prevent leakage at high operating pressure.

2. The liquid chromatography column according to claim 1 wherein the first end of each of said end fittings has a seat and wherein said column further comprises a biocompatible frit held within each of the seats in said end fittings.

3. The liquid chromatography column according to claim 2 wherein one of said end fittings and said inner tube comprise a unitary piece.

4. The liquid chromatography column according to claim 1 wherein the second end of each of said end fittings is tapered so that the outside diameter of the end fitting decreases towards the second end of said end fitting.

5. The liquid chromatography column according to claim 1 wherein the second end of each of said end fittings comprises a port adapted for connection in a liquid chromatography system.

6. The liquid chromatography column according to claim 1 wherein said inner tube comprises polyetheretherketone.

7. The liquid chromatography column according to claim 1 wherein said metal outer tube comprises stainless steel.

8. The liquid chromatography column according to claim 1 wherein said metal outer tube comprises aluminum.

9. The liquid chromatography column according to claim 1 wherein said inner tube consists of polyetheretherketone.

10. The liquid chromatography column according to claim 1 wherein said end fittings comprise polyetheretherketone.

11. The liquid chromatography column according to claim 1 further comprising a packing material located within the passageway of said inner tube.

12. The liquid chromatography column according to claim 11 wherein said packing material comprises octadecyl.

13. The liquid chromatography column according to claim 11 wherein said packing material comprises octyl.

14. The liquid chromatography column according to claim 11 wherein said packing material comprises silica.

15. A column for liquid chromatography which comprises:

an outer metal tube having first and second ends;

a biocompatible inner tube having a passageway therethrough sized and dimensioned for retaining chromatographic packing material and having first and second ends, wherein said inner tube is located within said outer metal tube and the passageway through said inner tube contains a packing material;

first and second biocompatible end fittings that allows for connection to a chromatography system each having a passageway therethrough and each having a first and second end, wherein the first end of each of said end fittings abuts an end of said inner tube and the second end of each of said end fittings extends beyond the end of said outer tube, and wherein the first end of each end fitting has a counterbore seat; and biocompatible frits located within the seats of the end fittings; and wherein the ends of the outer tube are tapered to extend inward towards the longitudinal axis of the outer tube at an angle sufficient to hold said first and second end fittings in place, thus holding said frits and said inner tube in place within the outer tube and prevent leakage at high operating pressure.

16. A guard column for liquid chromatography which comprises:

an stainless steel outer tube having an inside surface and having first and second ends;

a biocompatible inner tube having a passageway sized and dimensioned for retaining chromatographic packing material therethrough and having first and second ends, wherein said inner tube is located within said outer tube;

first and second biocompatible end fittings located at least partially within said outer tube, with each end fitting that allows for connection to a chromatography system having a passageway therethrough and each having a first and second end, wherein the-first end of each of said end fittings abuts an end of said inner tube and the second end of each of said end fittings extends beyond the end of said outer tube, and wherein the first end of each end fitting has a counterbore seat;

a packing material located within the inner tube; and a biocompatible frit located within the seat of each of the end fittings; and wherein the ends of the outer tube are tapered to extend radially inward towards the longitudinal axis of the outer tube at an angle sufficient to hold said first and second end fittings in place, thus holding said frits and said inner tube in place within the outer tube and prevent leakage at high operating pressure.

17. The liquid chromatography column according to claim 16 wherein the second end of each of said end fittings is tapered so that the diameter of the end fitting decreases towards the second end of said end fitting.

18. The liquid chromatography column according to claim 17 wherein the second end of each of said end fittings comprises a port adapted for connection in a liquid chromatography system.

* * * * *